US00PP12039P2

(12) United States Plant Patent
Cornelis

(10) Patent No.: US PP12,039 P2
(45) Date of Patent: Aug. 7, 2001

(54) SPATHIPHYLLUM PLANT NAMED 'KALYPSO'

(75) Inventor: Daniel Cornelis, Merelbeke-Melsen (BE)

(73) Assignee: Milestone Agriculture, Inc., Apopka, FL (US)

( * ) Notice: Subject to any disclaimer, the term of this patent is extended or adjusted under 35 U.S.C. 154(b) by 0 days.

(21) Appl. No.: 09/561,015

(22) Filed: Apr. 28, 2000

(51) Int. Cl.[7] ..... A01H 5/00

(52) U.S. Cl. ..... Plt./364

(58) Field of Search ..... Plt./364

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Spathiphyllum plant named 'Kalypso', characterized by its large upright plant habit; large, rounded, dark green, shiny leaves; rapid growth rate; freely flowering; large rounded white spathes that are positioned above and beyond the foliage on strong peduncles; freely flowering; and long-lasting spathes.

1 Drawing Sheet

BACKGROUND OF THE INVENTION

The present Invention relates to a new and distinct cultivar of Spathiphyllum hybrid plant, botanically known as Spathiphyllum, and hereinafter referred to by the cultivar name 'Kalypso'.

The new cultivar is a product of a planned and controlled breeding program conducted by the Inventor in Merelbeke-Melsen, Belgium. The objective of the breeding program is to create early-flowering spathiphyllum cultivars with large rounded leaves. The new cultivar originated from a deliberate cross by the Inventor in 1997 of the Spathiphyllum cultivar 'Stephanie', disclosed in U.S. Plant Pat. No. 9,943, as the female or seed parent and the Spathiphyllum cultivar 'Daniel', disclosed in U.S. Plant Pat. No. 8,655, as the male or pollen parent. The cultivar 'Kalypso' was discovered and selected by the Inventor as a plant within the progeny of the stated cross in a controlled environment in Merelbeke-Melsen, Belgium.

Compared to plants of the female parent, the culitvar 'Stephanie', plants of the new Spathiphyllum are smaller, have more rounded leaves and are more tolerant to high temperatures. Compared to plants of the male parent, the cultivar 'Daniel', plants of the new Spathiphyllum are larger, faster growing, have broader leaves and larger spathes.

Asexual propagation of the new cultivar by tissue culture in a laboratory in Belgium has shown that the unique features of this new Spathiphyllum plant are stable and reproduced true to type in successive generations of asexual propagation.

SUMMARY OF THE INVENTION

The new Spathiphyllum has not been observed under all possible environmental conditions. The phenotype may vary somewhat with variations in environment such as temperature, light intensity, fertilizer level and propagation procedures, without, however, any variance in genotype.

The following traits have been repeatedly observed and are determined to be the unique characteristics of 'Kalypso'. These characteristics in combination distinguish 'Kalypso' as a new and distinct cultivar:

1. Large upright plant habit.
2. Large, rounded, dark green, shiny leaves.

3. Rapid growth rate.
4. Freely flowering.
5. Large rounded white spathes that are positioned above and beyond the foliage on strong peduncles.
6. Freely flowering.
7. Long-lasting spathes.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new Spathiphyllum. The photograph comprises a side perspective view of a typical plant of 'Kalypso' in a 20-cm container.

DETAILED BOTANICAL DESCRIPTION

The following observations, measurements and comparisions describe 30-week old plants (from microcuttings) grown in Apopka, Fla., during the spring, under commercial greenhouse conditions in 20-cm containers. Day temperatures ranged from 24 to 32° C. and night temperatures ranged from 18 to 24° C. Light level was about 1,500 foot-candles.

In the following description, color references are made to The Royal Horticultural Society Colour Chart except where general terms of ordinary dictionary significance are used.

Botanical classification: Spathiphyllum hybrid cultivar 'Kalypso'.

Parentage:

*Female parent.*—Spathiphyllum cultivar 'Stephanie', disclosed in U.S. Plant Pat. No. 9,943.

*Male parent.*—Spathiphyllum cultivar 'Daniel', disclosed in U.S. Plant Pat. No. 8,655.

Propagation:

*Type.*—By tissue culture.

*Time to initiate roots.*—Summer: About 30 days at 24° C. Winter: About 45 days at 21° C.

*Time to develop roots.*—Summer: About 70 days at 24° C. Winter: About 80 days at 21° C.

*Root description.*—Freely branching, numerous fleshy roots.

Plant description:

*Plant shape.*—Upright, inverted triangle, symmetrical.

*Growth habit.*—Erect when young, becoming outwardly arching as leaves develop. Freely clumping with numerous new shoots; full and bushy appearance. Appropriate for 20-cm containers.

*Plant height.*—About 70 cm from soil level to top of leaf plane.

*Plant spread.*—About 82 cm.

*Plant vigor.*—Vigorous, rapid growth rate.

*Crop time.*—About 30 weeks are required to produce a finished flowering plant in 20-cm container from a tissue-cultured microcutting.

*Foliage description.*—Length: About 31 cm. Width: About 17.5 cm. Shape: Broadly ovate. Apex: Elongated acuminate. Base: Obtuse. Margin: Entire, undulate. Aspect: Initially upright, then somewhate reflexed. Surface: Rugose; midrib and lateral veins, sunken. Texture: Leathery, smooth, glabrous, very durable; flexible; both surfaces glossy. Color: Young, upper surface: Greener and lighter than 147A. Young, lower surface: Close to 147B. Mature, upper surface: Close to 147A. Mature, lower surface: Greener than 147B. Petiole: Aspect: Initially erect to about 45° to vertical with development; geniculum, bent. Length: About 37 cm. Diameter, base: About 1.5 cm. Diameter, above geniculum: About 5.5 mm. Strength: Strong, flexible. Color: Below and above geniculum, between 144A and 146A; geniculum, close to 144A. Wing length: About 23 cm. Wing diameter: About 9 mm. Geniculum length: About 3.8 cm. Geniculum diameter: About 7 mm.

Inflorescence description:

*Inflorescence arrangement.*—Concave spathes with spadices held above and beyond the foliage on strong peduncles. Freely flowering; inflorescences arise from leaf axils.

*Inflorescence longevity.*—Inflorescences are long-lasting, generally maintaining white color for about two months on the plant depending on light and temperature levels.

*Fragrance.*—Slight, typical of Spathiphyllum.

*Spathe.*—Length: About 17.5 cm. Width: About 11.5 cm. Shape: Rounded ovate. Apex: Elongated acuminate. Base: Obtuse. Aspect: Concave, curling over the spadix. Color (Both surfaces): White, 155A, becoming green, close to 144A, with development.

*Spadix.*—Length: About 5.8 cm. Diameter: About 1.7 cm. Color: 158D becoming green, 144B to darker than 143A, with development. Quantity of flowers: About 300. Pollen: White, close to 155A.

*Peduncle.*—Aspect: Strong. Length: About 51 cm. Diameter: About 7 mm. Color: Close to 144A.

*Seed.*—Seed development has not been observed.

Disease resistance: Plants of the new Spathiphyllum have exhibited good resistance to pathogens common to Spathiphyllum.

Temperature tolerance: Plants of the new Spathiphyllum have been shown to tolerate temperatures from 6 to 37° C.

It is claimed:

1. A new and distinct cultivar of Spathiphyllum plant named 'Kalypso', as illustrated and described.

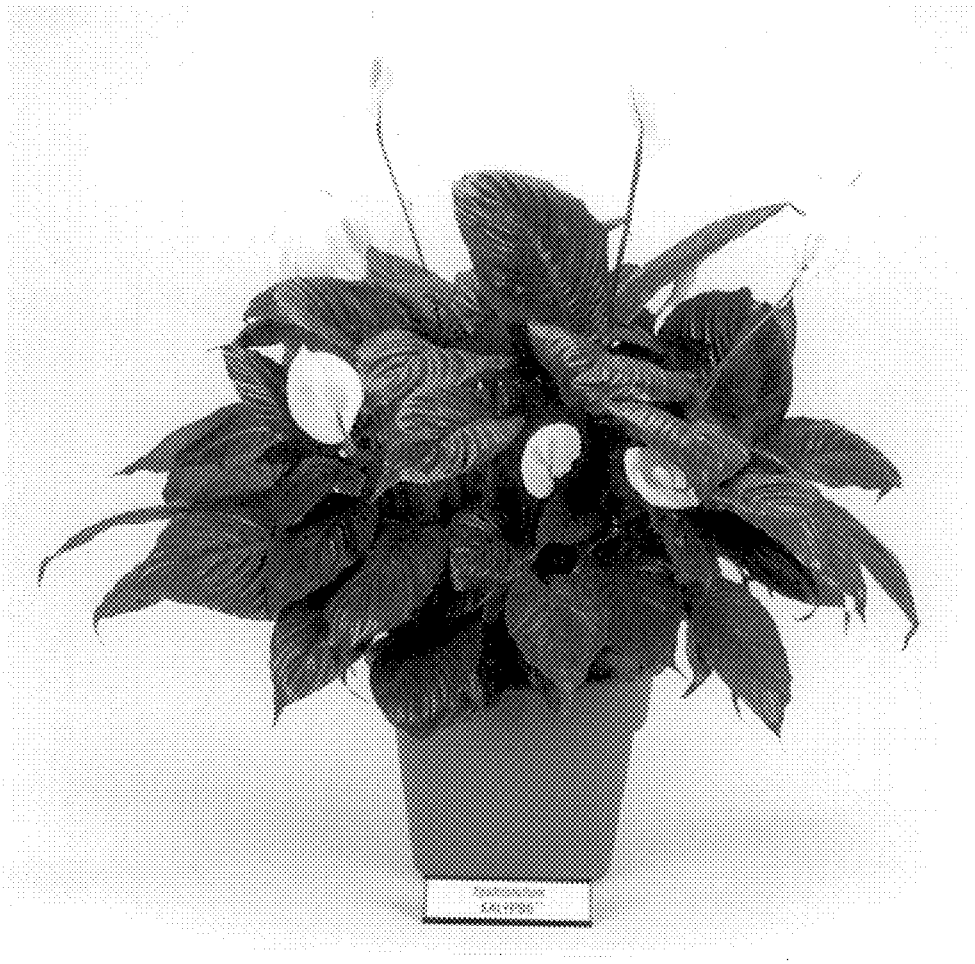

* * * * *